United States Patent [19]
Kazan

[11] 3,944,616
[45] Mar. 16, 1976

[54] PURIFICATION OF D,D'-2,2'(ETHYLENEDIIMINO)DI-1-BUTANOL DIHYDROCHLORIDE

[75] Inventor: John Kazan, Somerville, N.J.

[73] Assignee: American Cyanamid Company, Stamford, Conn.

[22] Filed: Oct. 29, 1974

[21] Appl. No.: 518,832

[52] U.S. Cl............................................ 260/584 R
[51] Int. Cl.²................... C07C 89/00; C07C 89/04
[58] Field of Search ................................ 260/584 R

[56] References Cited
UNITED STATES PATENTS

| | | | |
|---|---|---|---|
| 2,569,549 | 10/1951 | Barrick ........................ | 260/584 R X |
| 3,176,040 | 3/1965 | Wilkinson et al. ........... | 260/584 R X |
| 3,553,257 | 1/1971 | Halmas ........................ | 260/584 R X |
| 3,579,586 | 5/1971 | Loja .............................. | 260/584 R |
| 3,579,587 | 5/1971 | Loja .............................. | 260/584 R |
| 3,769,347 | 10/1973 | Kazan ........................... | 260/584 R |
| 3,855,300 | 12/1974 | Takahashi et al. ............ | 260/584 R |

OTHER PUBLICATIONS
J.A.C.S., V76, pp. 2801–2803 (1954).
J.A.C.S., V83, pp. 2212–2213 (1961).
Chemical Abstracts, V79, 65780e (1973).

*Primary Examiner*—Helen M. S. Sneed
*Attorney, Agent, or Firm*—Samuel Branch Walker

[57] ABSTRACT

A superior grade of d,d'-2,2'-(ethylenediimino)di-1-butanol dihydrochloride from the reaction of ethylene dichloride and an excess of d-2-amino-1-butanol is obtained by mixing finely divided sodium hydroxide with the reaction mixture, vacuum distilling off d-2-amino-1-butanol, adding a 2-4 carbon alkanol, preferably isopropanol, separating sodium chloride, adding water or an aqueous 2-4 carbon alkanol thereto to a water content of about 7-10% by weight, and an essentially stoichiometric amount of hydrogen chloride, to precipitate d,d'-2,2'-(ethylenediimino)di-1-butanol dihydrochloride, cooling the reaction mixture, and separating a pharmaceutical grade product.

4 Claims, No Drawings

PURIFICATION OF D,D'-2,2'(ETHYLENEDIIMINO)DI-1-BUTANOL DIHYDROCHLORIDE

SUMMARY OF THE INVENTION

This invention relates to improvements in the synthesis of d,d'-2,2'-(ethylenediimino)di-1-butanol dihydrochloride (ethambutol hydrochloride).

Ethambutol, usually administered as the hydrocloride, is a therapeutic agent for the treatment of tubercle bacilli infections, particularly human tuberculosis caused by *Mycobacterium tuberculosis*. The compound, its preparation, and its therapeutic use are disclosed in U.S. Pat. No. 3,176,040, 1965, Wilkinson and Sheperd, see Example 2 thereof. The improved therapeutic activity of the d,d'-isomer is reported in J. Am. Chem. Soc. 83, 2212 (1961).

$$ClCH_2CH_2Cl + 2CH_3CH_2\underset{NH_2}{C}HCH_3OH \rightarrow$$

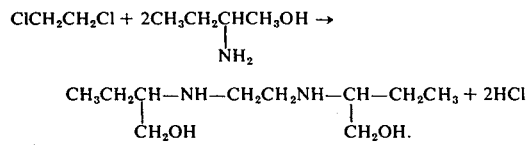

One method of resolving aminobutanol is disclosed in U.S. Pat. No. 3,553,257, Jan. 5, 1971, Halmos and Ricketts.

The production of ethambutol hydrochloride at a minimum cost, with pharmaceutically acceptable purity, including a high decomposition temperature, freedom from ash, proper optical rotation characteristics, and in an economical yield, is the subject of research programs.

U.S. Pat. No. 3,769,347, Oct. 30, 1973, Kazan, the full disclosure of which is hereby herein incorporated by this reference thereto, discloses a process for preparing d,d'-2,2'-(ethylenediimino)di-1-butanol dihydrochloride by reacting liquid ethylene dichloride with liquid d-2-amino-1-butanol to form a mixture of d,d'-2,2'-(ethylenediimino)di-1-butanol, d-2-amino-1-butanol and the hydrochloride salts thereof including:

1. mixing an excess of d-2-amino-1-butanol which acts as solvent as well as reactant, with ethylene dichloride, and causing the mixture to react,
2. adding to the mixture sufficient finely divided sodium hydroxide to react with the hydrogen chloride present to form sodium chloride,
3. vacuum distilling off and separating the unreacted d-2-amino-1-butanol from the mixture, for recycle to subsequent batches,
4. adding a 2 to 4 carbon alkanol, to form a solution of d,d'-2,2'-(ethylenediimino)di-1-butanol in the alkanol,
5. separating the undissolved sodium chloride from the solution,
6. adding hydrogen chloride gas to the resulting solution to form d,d'-2,2'-(ethylenediimino)di-1-butanol dihydrochloride, as a precipitate, and
7. separating the precipitate of d,d'-2,2'-(ethylenediimino)di-1-butanol dihydrochloride from the alkanol.

The proces of Kazan usually results in a product having a decomposition range of 198.5°–204°C. which is pharmaceutically acceptable. Depending on impurities in the starting materials and normal plant variations from a designed program, about 1 in 5 batches made by this process need to be recrystallized to maintain a decomposition range of at least 198.5°–204°C.

It has now been found that a product having a decomposition range starting at least at 200°C. is obtained consistently in equal or improved yields by synthesizing the ethambutol dihydrochloride and precipitating the same in a 2 to 4 carbon alkanol solution, or mixture of these alkanols, containing about 7 to 10% by weight of water on the total weight of the reaction mixture.

The process of the present invention is distinguished from the process of U.S. Pat. No. 3,769,347 in that 1. the formation of the ethambutol dihydrochloride and the precipitation of the same is carried out in a 2 to 4 carbon alkanol, or mixture of these alkanols, containing about 7 to 10% by weight of water instead of about 2 to 3% by weight of water,
2. the hydrogen chloride and water may be added to the reaction mixture simultaneously as concentrated hydrochloric acid, and
3. the isolation of the product is carried out at 0° to −10°C. instead of at ambient conditions.

In the present invention, the prior art process of U.S. Pat. No. 3,769,347 is followed through step (5). The improvement occurs in that hydrogen chloride may be added as a concentrated aqueous solution, and the presence of 7 to 10% water improves the purity of product.

The filtrate from step (5) is diluted with either a 2 to 4 carbon alkanol, preferably isopropanol, or a 2 to 4 carbon aqueous alkanol, preferably aqueous isopropanol, using up to ⅓ part by volume of diluent per part by volume of filtrate. The diluted solution is then heated to 40°–60°C., preferably 50°–55°C.

If the alkanol diluent used is anhydrous, sufficient concentrated aqueous hydrochloric acid is added to the solution to convert all of the d,d'-2,2'-(ethylenediimino)di-1-butanol to the dihydrochloride salt, plus a small excess of acid. Concentrated hydrochloric acid as disclosed herein is defined as an aqueous solution containing 36–38%, preferably about 37%, by weight of hydrogen chloride. After the addition of the concentrated hydrochloric acid the reaction mixture contains 7–10%, preferably 8–9%, by weight of water, on the total weight of the reaction mixture.

If the diluent used is an aqueous alkanol sufficient hydrogen chloride gas is added to the clear solution to convert all of the d,d'-2,2'-(ethylenediimino)di-1-butanol to the dihydrochloride salt, plus a small excess. Conveniently, the hydrogen gas is introduced over the surface of the solution in a closed vessel while maintaining a pressure of about 5–7 psi g. in the vessel. During the addition of the hydrogen chloride gas, the temperature should be maintained about 40°–60°C., preferably about 50°–55°C. After the addition of the hydrogen chloride gas the reaction mixture should contain 7–10%, preferably about 8–9%, by weight of water, on the total weight of the reaction mixture.

Conveniently, before adding either the concentrated hydrochloric acid, or the hydrogen chloride gas, a small aliquot of the solution is titrated to determine the quantity of acid or gas required.

The reaction mixture is slowly cooled over about 3 hours to about 0° to −10°C. preferably about 0° to −5°C. It should test acid to Congo Red indicator paper. The crystalline precipitate of d,d'-2,2'-(ethylenediimino)di-1-butanol dihydrochloride is separated by filtration at a temperature of 0° to −10°C., preferably 0° to −5°C. The crystals are washed with a 2 to 4 carbon alkanol at ambient temperatures and dried at a temperature below about 80°C.

The use of a single alkanol, preferably isopropanol, in the isolation procedures permits more economical recovery and recycle of the solvent. With the current stress on ecological improvements, separating the isopropanol in a readily recoverable form is advantageous. If separated as a mixture with water and methanol, recycling is far more complex than when the mother liquor is isopropanol and water. A conventional azeotropic distillation permits recycling of essentially pure anhydrous isopropanol. Depending on cost factors in a particular establishment, it may be more economical to use isopropanol containing some water as the solvent, and add at least part of the hydrogen chloride as an anhydrous gas, rather than use aqueous hydrochloric acid to achieve the same final concentrations for the isolation of the d,d'-2,2'-(ethylenediimino)di-1-butanol dihydrochloride.

Centrifugation or other solid liquid separation procedure may be used instead of filtration, if plant equipment therefor is more conveniently available, at any step where solid liquid separation is desired.

The final product has a decomposition range starting at least at 200°C., an assay of not less than 99%, an ash content of not more than 0.1% and a specific rotation (10.0% in water) of not less than 6.0°.

The invention is illustrated by the following examples in which parts are by weight unless otherwise clearly indicated.

EXAMPLE I

Synthesis of d,d'-2,2'-(ethylenediimino)di-1-butanol

The following example illustrates the preparation of ethambutol as the free base, using the procedure disclosed in U.S. Pat. No. 3,769,347, supra.

1. A mixture of 4620 g. of d-2-amino-1-butanol and 320 g. of ethylene dichloride is heated to 80°C. and the temperature is allowed to rise exothermally to about 130°C. After 1 hour, the mixture is cooled to about 95°C., 225 g. of sodium hydroxide is slowly added, and a temperature of about 112°C. is maintained for 1 hour. The sodium hydroxide is in the form of prills of about 4 mm. diameter. The mixture is cooled to 70°C. and unreacted d-2-amino-1-butanol is recovered by vacuum distillation. The distillation is at a pressure below 20 mm. mercury, and below 130°C., heat being applied at a rate within the capacity of the condenser.

2. Isopropanol (2900 g.) is added to the distillation residue at a temperature not above about 90°C., and followed by a refluxing period of 30 minutes. The mixture is cooled to and filtered at 60°C. to remove sodium chloride, and the filter cake is washed with 470 g. of isopropanol, at 60°C. The volume of the filtrate is diluted to 4700 ml. with isopropanol and the temperature is adjusted to 40°–45°C., 15 g. of diatomaceous earth filter aid is added, and a second filtration is carried out. The filtrate is labeled "filtrate A."

EXAMPLE II

Conventional Isolation of Dihydrochloride

1. To 470 ml. of filtrate A are added 150 ml. of methanol and 18 ml. of water in a reaction vessel. The vessel is closed and hydrogen chloride gas (about 26.5 g.) is introduced over the surface of the reaction mixture at a gas pressure of 5–7 psi g. while the temperature is allowed to rise to 52°–60°C., until precipitation is completed. The reaction mixture is cooled over a period of 3 hours to 18°C.

2. Conveniently, a small aliquot is titrated, and a calculated quantity of hydrogen chloride added. Proper final pH is confirmed by testing as acid to wet Congo Red test paper. The white crystalline product, d,d'-2,2'-(ethylenediimino)-di-1-butanol of dihydrochloride is separated by filtration, and washed with 230 ml. of isopropanol.

The product, after carefully drying at a maximum temperature of 80°C., is about 68.5 g., having a decomposition range of 198.3°–201.5°C. and an ash content of less than 0.1%

EXAMPLE III

Aqueous Hydrochloric Acid Usage

To 470 ml. of filtrate A of Example I are added 150 ml. of methanol in a reaction vessel and the mixture is heated to 50°C. and 73.5 g. of 36% aqueous hydrochloric acid are added dropwise over a period of ¼ hour while allowing the temperature to rise to 56°C. The reaction mixture is cooled to −10°C. over a period of 3 hours and held at −10°C. for ½ hour. The reaction mixture is then processed as in step (2) of Example II to obtain 65.2 g. of the desired product having a decomposition range of 200.8°–203.3°C. and an ash content of less than 0.1%.

The use of aqueous hydrochloric acid results in a higher decomposition temperature, and a superior product.

EXAMPLE IV

Aqueous hydrochloric Acid and Single Solvent

To 470 ml. of filtrate A of Example I are added 150 ml. of isopropanol in a suitable reaction vessel and the mixture is heated to 50°C. and 73.5 g. of 36% hydrochloric acid are added dropwise as in Example III. The reaction mixture is then cooled and processed as in Example III to obtain 67.0 g. of the desired product having a decomposition point of 200.5°C–203.0°C and an ash content of less than 0.1%.

As only isopropanol and water are used in the separation, the mother liquor is readily azeotropically distilled to permit recycling of the isopropanol to a later batch.

EXAMPLE V

Gaseous Hydrogen Chloride to an Aqueous System

To 470 ml. of filtrate A of Example I is added 150 ml. of isopropanol and 47.0 g. of water in a reaction vessel. The vessel is closed and the mixture is heated to 50°C. and hydrogen chloride gas (about 26.5 g.) is introduced over the surface of the charge at a gas pressure of 5–7 psi g., while the temperature is maintained at 50°–55°C. over a period of ¼ hour. The charge is cooled slowly to −10°C. over a period of 3 hours and held at −10°C. for ½ hour. The reaction mixture is then removed from the reactor and processed thereafter as in Example III. A product of equal quality is obtained.

While an explanation of the improved purity is not certain, it would appear that the 7 to 10% water aids in solubilization of any residual sodium chloride, or other inorganic salt, as well as in by-products including polymers from the reaction of ethylene dichloride with the secondary amine groups in the d,d'-2,2'-(ethylenediimino)di-1-butanol. Impurities in starting materials, particularly undesired optical isomers, may introduce other undesired components whose elimination is aided by the aqueous component in the crystallizing alkanol.

I claim:
1. In a process for preparing d,d'-2,2'-(ethylenediimino)di-1-butanol dihydrochloride comprising the steps of reacting excess d-2-amino-1-butanol with ethylene dichloride, adding to the reaction mixture thus formed sufficient finely divided sodium hydroxide to neutralize hydrogen chloride formed therein, distilling off unreacted d-2-amino-1-butanol, adding sufficient of a 2 to 4 carbon alkanol to the residue to dissolve the thus formed d,d'-2,2'-(ethylenediimino)di-1-butanol, separating sodium chloride therefrom, adding hydrogen chloride to the resulting solution to form d,d'-2,2'-(ethylenediimino)di-1-butanol dihydrochloride, and separating the same from said alkanol, the improvement which comprises:

reacting a 2 carbon alkanol solution of d,d'-2,2'-(ethylenediimino)di-1-butanol with an essentially stoichiometric amount of hydrogen chloride at 40°–60°C. in the presence of about 7% to 10% by weight water, based on the total weight of the reaction mixture to form d,d'-2,2'-(ethylenediimino)di-1-butanol dihydrochloride, slowly cooling the resulting aqueous alkanol solution to 0 to −10°C. to precipitate said dihydrochloride, separating said dihydrochloride from said aqueous alkanol solution, washing said dihydrochloride with a 2 to 4 carbon alkanol, and drying the same.

2. The process of claim 1 in which the 2 to 4 carbon alkanol solution is isopropanol.

3. The process of claim 2 in which the isopropanol solution is formed by adding 36–38% aqueous hydrogen chloride to a solution of d,d'-2,2'-(etylenediimino)di-1-butanol in isopropanol.

4. The process of claim 2 in which the 7 to 10% aqueous isopropanol solution is formed by adding aqueous isopropanol to a solution of d,d'-2,2'-(ethylenediimino)di-1-butanol in isopropanol and said hydrogen chloride is added as a gas.

* * * * *

UNITED STATES PATENT OFFICE
CERTIFICATE OF CORRECTION

Patent No. 3,944,616　　　　　Dated　March 16, 1976

Inventor(s)　John Kazan

It is certified that error appears in the above-identified patent and that said Letters Patent are hereby corrected as shown below:

Column 5, line 23 "reacting a 2 carbon" should read
-- reacting a 2 to 4 carbon --.

Column 6, line 18 "etylenediimino" should read -- ethylenediimino --.

Signed and Sealed this fifteenth Day of June 1976

[SEAL]

Attest:

RUTH C. MASON
Attesting Officer

C. MARSHALL DANN
Commissioner of Patents and Trademarks